United States Patent [19]
Li

[11] Patent Number: 5,836,990
[45] Date of Patent: Nov. 17, 1998

[54] METHOD AND APPARATUS FOR DETERMINING ELECTRODE/TISSUE CONTACT

[75] Inventor: Hong Li, Cupertino, Calif.

[73] Assignee: Medtronic, Inc., Minneapolis, Minn.

[21] Appl. No.: 934,286

[22] Filed: Sep. 19, 1997

[51] Int. Cl.⁶ .................................................. A61N 1/08
[52] U.S. Cl. ............................................................ 607/28
[58] Field of Search ........................ 607/28, 72; 600/372, 600/373, 374, 547

[56] References Cited

U.S. PATENT DOCUMENTS

| | | |
|---|---|---|
| 3,320,946 | 5/1967 | Dethloff et al. . |
| 3,949,736 | 4/1976 | Vrana et al. . |
| 3,971,365 | 7/1976 | Smith . |
| 4,245,643 | 1/1981 | Benzing et al. ............................ 607/28 |
| 5,078,678 | 1/1992 | Katims . |
| 5,233,515 | 8/1993 | Cosman . |
| 5,427,113 | 6/1995 | Hiroshi et al. . |
| 5,553,611 | 9/1996 | Budd et al. . |
| 5,578,064 | 11/1996 | Prutchi . |
| 5,649,969 | 7/1997 | Abrahamson et al. .................... 607/28 |

*Primary Examiner*—Scott M. Getzow
*Attorney, Agent, or Firm*—Townsend and Townsend and Crew LLP

[57] ABSTRACT

Contact between an electrophysiology catheter electrode (6) and cardiac tissue covered by blood is sensed by applying a constant voltage or current square wave signal (23) to the electrode and then monitoring the voltage or impedance or current at the electrode before, during, and after the electrode contacts the tissue. The monitored pulse (22) includes an ohmic impedance portion (30) and combined ohmic and capacitive impedance portion (32). Successive monitored pulses can be measured in several ways to determine when tissue contact has occurred: the maximum magnitudes (36) of successive ohmic resistance portions; the initial slopes (38) for successive combined resistive portions; the amplitudes (40) of successive combined resistive portions at a preset time interval from the start of each pulse; and the average amplitudes (42) of successive combined impedance portions over a preset time period for each pulse. Upon contact, the magnitudes of each changes significantly, such as 40–50% in cardiac applications.

29 Claims, 3 Drawing Sheets

METHOD AND APPARATUS FOR DETERMINING ELECTRODE/TISSUE CONTACT

BACKGROUND OF THE INVENTION

Catheters with electrodes at their tips are commonly used for various therapeutic and diagnostic purposes. It is usually important to know when the electrode makes contact with the tissue at the target site. For example, using an electrophysiology catheter to perform RF ablation on cardiac tissue, providing pacing signals to cardiac tissue or sensing electrophysiological signals within cardiac tissue, knowing when the electrode comes into contact with the tissue at the target site is very important. If the electrode is spaced apart from the target tissue, poor ablation, poor pacing, or poor sensing can occur. This due at least in part to the fact that blood is a much better electrical conductor than cardiac tissue.

SUMMARY OF THE INVENTION

The present invention provides a relatively simple, effective and safe method for accurately and quickly determining when an electrode, typically carried by an electrophysiology catheter, has contacted the target tissue within a patient, typically within the heart.

Contact between an electrode and tissue, typically an electrophysiology catheter electrode and cardiac tissue, is achieved by applying a pulsed signal, having a series of signal pulses, each signal pulse having a leading edge portion and a following portion, and then monitoring an electrical characteristic, typically the voltage or impedance or current, at the electrode during a period of time before, during, and after the electrode contacts the tissue. The initial rise corresponds to the ohmic impedance portion of each signal pulse; this is followed by a second, or following, ohmic and capacitive impedance portion of each signal pulse. The voltage or impedance or current is typically monitored in one of four different ways to determine when tissue contact has occurred. The first is to measure the voltage or impedance or current of the first portions for successive pulsed signals. A second way is to measure the slope of the voltage or impedance or current for an initial part of the following portions for successive pulsed signals. A third way is to measure the amplitude of the pulse at a pre-set time interval from the leading edge. A fourth way is to measure the average amplitude over a pre-set time period of the pulse. Upon contact, readings from each of these four measuring methods increase significantly, such as 40–50%. The third method is preferred when the time is optimally pre-set. These monitoring techniques can be done manually or automatically.

The present invention is based on the fact that tissue, such as cardiac tissue, has a significantly higher electrical impedance than an ionic fluid, such as blood, contacting the tissue.

The present invention provides several advantages, including the ability to provide the physician or other user with a substantially instantaneous determination of when tissue contact has occurred without affecting normal heart activity or sensing. Also, the apparatus is relatively easy to make and use.

A constant current DC pulse (at least about 0.1 ma, preferably about 1–10 ma in amplitude; about 1 $\mu$sec–2 msec in duration; repeated at least about 0.1 Hz and preferably about 1–5 Hz) is preferably used as the pulse for cardiac techniques. By using a short pulse duration, such as less than about 50 $\mu$sec, and a low current, such as 10 ma, no stimulation of the heart will occur; it is therefore safe to use even though many signal pulses are applied. It is preferred that the pulsed signal generator be designed to limit the maximum voltage output for enhanced safety. Constant voltage DC pulse (at least about 0.1 v and preferably about 1–5 v; about 1 $\mu$sec–2 msec in duration; repeated at least about 0.1 Hz and preferably about 1–5 Hz) can also be used.

Using the constant current DC signal pulses is preferred over using other types of signals. For example, AC can cause fibrillation; radio frequency (RF) energy affects sensing and RF impedance is not very sensitive to tissue/electrode contact; low frequency AC impedance differences with and without contact can typically be less than 10%, which is much less than the difference in the voltage/impedance readings using constant current DC signal pulses.

The present invention is particularly useful to determine tissue/electrode contact during RF ablation of cardiac tissue. It can, however, be used in other situations and for other purposes. For example, it can be used to determine contact between an electrode and other body organs or tissue to be ablated, such as the prostate.

Other features and advantages will appear from the following description in which the preferred embodiment has been set forth in detail in conjunction with the accompanying drawings.

DESCRIPTION OF THE PREFERRED EMBODIMENT

Figure 1:
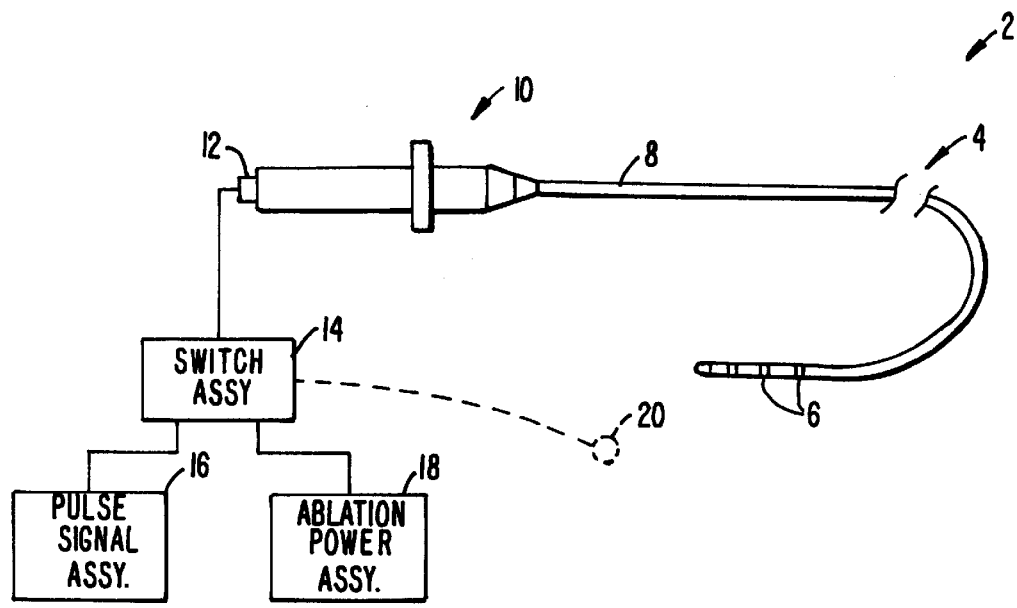
FIG. 1 is a simplified overall view of a cardiac ablation apparatus made according to the invention.

FIG. 1 is a simplified overall view of a cardiac ablation apparatus 2 made according to the invention. Apparatus 2 includes an ablation catheter 4 having a number of ablation electrodes 6 at the distal end of a catheter shaft 8 Ablation catheter 4 also includes a proximal end assembly or handle 10 used to manipulate the distal end of catheter shaft 8. Handle 8 includes an electrical connector 12 coupled to a switch assembly 14. Switch assembly 14 is used to electrically couple one or more electrodes 6 to either or both of a pulse signal assembly 16 or an ablation power assembly 18. When switch assembly 14 is in a unipolar mode, one or both of assemblies 16, 18 are coupled to one or more of ablation electrodes 6 and to an indifferent plate electrode 20 secured somewhere on the patient's skin. When switch assembly 14 is in a bipolar mode, one or more pairs of electrodes 6 will be coupled to one or both of assemblies 16, 18. The use of apparatus 2 will be discussed in more detail below with reference to FIG. 4.

Figure 1A:
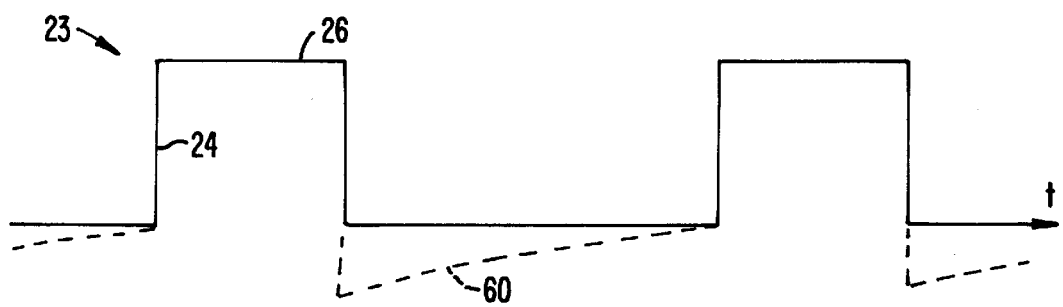
FIG. 1A illustrates a plot of either current or voltage versus the time for a constant current DC signal pulse or a constant voltage DC signal pulse applied to pure impedance.

FIG. 1A illustrates a plot of voltage or current versus time for a constant current DC signal pulse or current or impedance versus time for a constant current DC signal pulse when the signal pulse is applied to a pure impedance outside the body. The signal has a leading edge portion 24 and a following portion 26.

Figure 2:
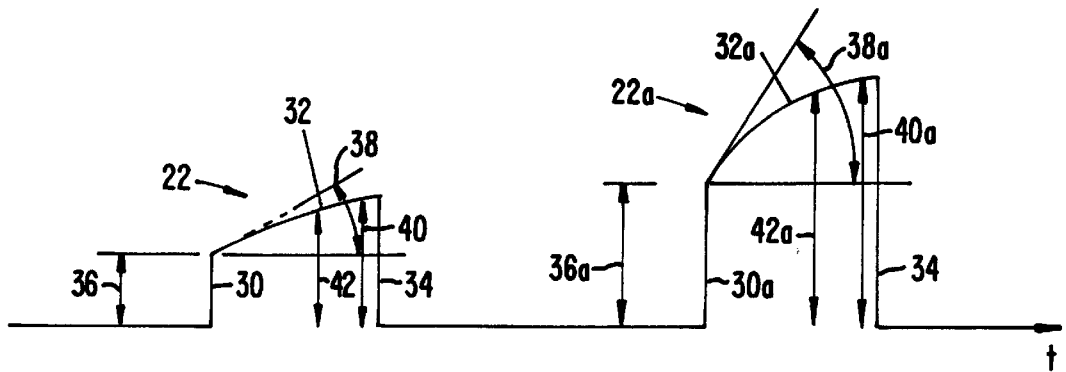
FIG. 2 illustrates the result of two constant current DC signal pulses in blood, the first monitored pulse being either voltage or impedance versus time prior to electrode contact with heart tissue and the second monitored pulse being either voltage or impedance versus time after electrode contact with heart tissue, the same basic monitored pulse shape being exhibited for constant voltage DC signal pulses with the plot being of impedance versus time.

FIG. 2 is a monitored plot of either voltage or impedance versus time for two pulses of a constant current DC signal pulse with ablation electrodes 6 within blood within a heart chamber before and after contact with heart tissue. That is, a first monitored pulse 22, on the left-hand side of the figure, plots the measured voltage or impedance versus time before the appropriate electrode (or electrodes) 6 contacts the heart tissue. The second monitored pulse 22a reflects the increased impedance of heart tissue over the impedance of blood. Monitored pulses 22, 22a provide the user with a distinct, easily recognized indication that contact has occurred.

There are at least four different electrode characteristics of monitored pulses 22, 22a which can be used to determine when contact has occurred. Assume we are dealing with a constant current DC signal pulse 23 and that we are measuring impedance versus time. The leading edge portion 24 of DC signal pulse 23 results in an initial rise 30 of monitored pulse 22 in the impedance versus time plot of FIG. 2 while the following portion 26 of constant current DC signal pulse 23 results in an upwardly curving, following impedance versus time portion 32 of monitored pulse 22. Portion 32 is followed by a falling portion 34.

The first characteristic we can measure and monitor is initial rise impedance 36 and 36a. The second way is to measure the change in the initial slopes 38, 38a of the following portions 32, 32a of successive monitored pulses 22, 22a. The third way is to measure the impedance 40, 40a at a chosen time following initial rise 30, 30a. Of course, the chosen time must be equal or less than the pulse width. Finally, the average impedance 42 of all or parts of following portions 32, 32a can be determined and compared between successive pulses. As shown in FIG. 2, each of these measurements provides significant differences, typically about. 40–50%, before and after contact.

The above has been described with FIG. 2 as a impedance versus time plot. If instead of impedance, voltage is measured, voltage would, of course, take the place of impedance in these comparisons. Similarly, if a constant voltage DC signal pulse 23 is used instead of the constant current DC signal pulse 23 of FIG. 1A, then the plot of impedance versus time would be similar to that shown in FIG. 2.

Figure 3:
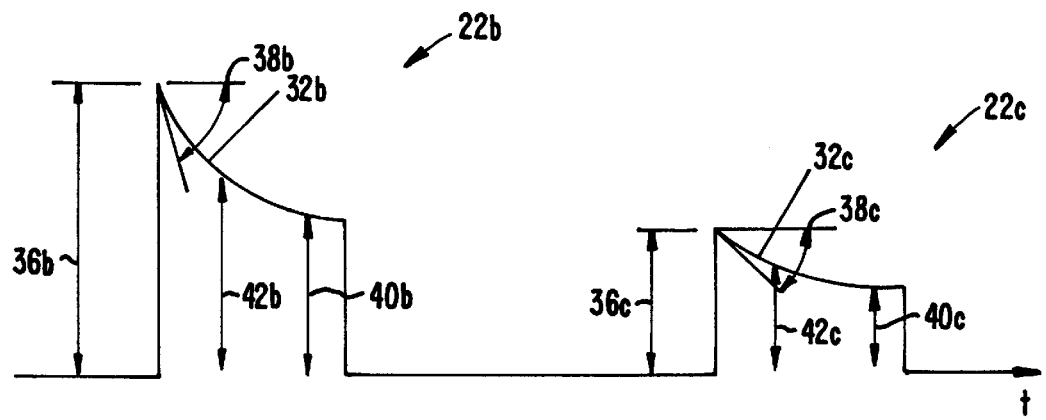
FIG. 3 illustrates a current versus time monitored pulse plot for a constant voltage DC signal pulse before and after contact with heart tissue, the second pulse reflecting the effect of the increased impedance of heart tissue as opposed to blood.

FIG. 3 illustrates the plot of current versus time when a constant voltage DC signal pulse 23 is applied to electrodes 6. Even though the plot for the current versus time monitored pulses 22b, 22c for the constant voltage DC signal pulse 23 is about the reverse of the plot of FIG. 2, the comparisons between the initial rise impedances 36b, 36c, initial slopes 38b, 38c, chosen time impedances 40b, 40c, and average impedances 42b, 42c are also very indicative of contact having occurred between electrodes 6 and a wall of the heart.

Figure 4:
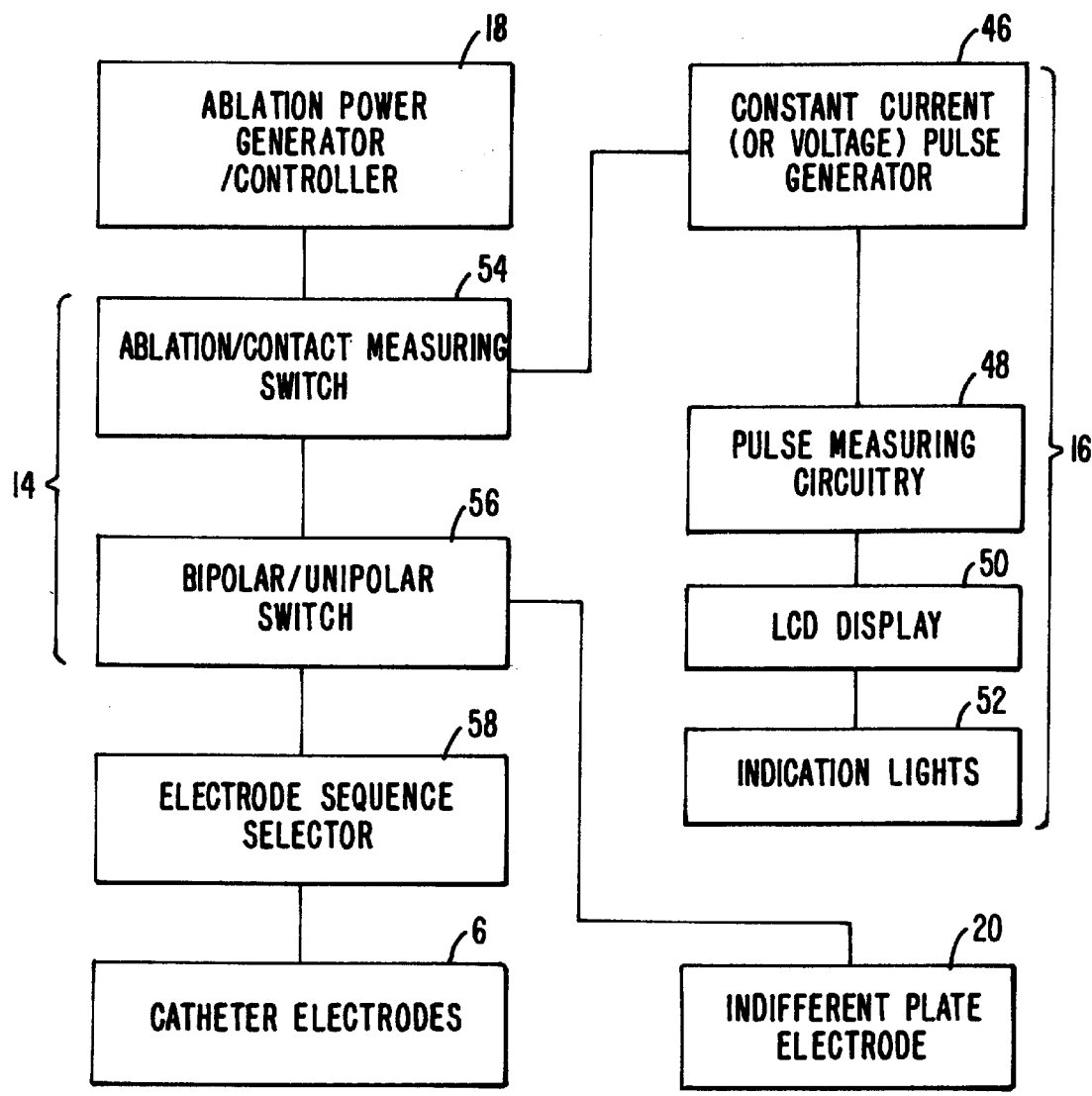
FIG. 4 is a schematic block diagram illustrating the logical arrangement of the components of a cardiac ablation apparatus made according to the invention.

FIG. 4 illustrates various components of the cardiac ablation apparatus 2 of FIG. 1. Pulse signal assembly 16 is seen to include a pulse generator 46 which generates the constant current or constant voltage DC signal pulse shown in FIG. 1A, pulse measuring circuitry 48 which measures the voltage, impedance, or current illustrated in the voltage or impedance versus time curve of FIG. 2 and the current versus time curve of FIG. 3. Assembly 16 also includes an LCD display 50 to display, in numbers, the measured quantities used to determine when contact has occurred. Specifically, and with reference to FIG. 2, LCD display 50 displays initial rise impedance 36, initial slope 38, chosen time impedance 40, and average impedance 42. In the preferred embodiment indication lights 52 are used to provide a simple indication to the operator when appropriate contact has been achieved. When the contact is good, that is, when contact has been made and maintained for a predetermined period of time, such as at least one pulse, a green light will be lit. When no contact occurs or when contact is poor, a red light will be on. When contact is intermittent, indicating that electrodes 6 are adjacent to the surface of the heart tissue but not positioned with sufficient force to ensure good electrical contact, the yellow light will be on. The parameters for when contact is good, poor, and intermittent can be adjustable by the user or fixed by the manufacturer.

Switch assembly 14 includes broadly an ablation/contact measuring switch 54 and a bipolar/unipolar switch 56. Switch 54 can be manipulated so that the switch couples one or both of ablation power assembly 18 and pulse generator 46 to bipolar/unipolar switch 56. As indicated above, switch 56 is used to couple switch 54 to either catheter electrodes 6 only or to both catheter electrodes 6 and indifferent plate electrode 20. FIG. 4 illustrates an additional element, electrode sequence selector 58 not shown in FIG. 1. Electrode sequence selector 58 selects one or more of electrodes 6 to be coupled to the appropriate signal or ablation source.

Impedance measurement is typically preferred over voltage or current measurement because impedance is independent of the pulse energy. In addition to LCD display 50, audible warnings indicating a loss of good contact could also be provided. When good contact is indicated by indication lights 52, ablation can be started by powering ablation power assembly 18 and, if necessary, proper actuation of switch 54. If desired, pulse generator 46 can be continued to be used during ablation so that contact can continue to be monitored because the signal pulse 23 is applied on top of the ablation energy signal. Alternatively, pulse signal assembly 16 can be turned off during actual ablation operations.

Modification and variation can be made to the disclosed embodiments without departing from the subject of the invention as defined in the following claims. For example, a recharge signal pulse 60, shown in dashed lines in FIG. 1A, can be used to balance each signal pulse 23 so to reduce electrical charges near electrode surface, which can affect measurement when high. Also, the invention has been described when the fluid, typically blood, covering the target site is more electrically conductive than the target site tissue, typically a chamber wall of a heart. The invention could be carried out when the fluid is less conductive than the target tissue or wall.

What is claimed is:

1. A method for determining electrode/tissue contact comprising the following steps:

choosing a constant current pulsed signal or a constant voltage pulsed signal, said chosen pulsed signal comprising a series of signal pulses;

applying said series of signal pulses to an electrode, each said signal pulse having a leading edge portion and a following portion;

placing the electrode into contact with a tissue site;

the placing step taking place with an ionic liquid covering the tissue site; and determining when the electrode contacts the tissue by monitoring a chosen electrical characteristic at the electrode during a period of time before, during, and after the electrode contacts the tissue.

2. The method according to claim 1, wherein the signal choosing step is carried out by choosing a constant voltage pulsed signal as the pulsed signal.

3. The method according to claim 2 wherein the monitoring step is carried out by monitoring at least one of current or impedance as the chosen electrical characteristic.

4. The method according to claim 2 wherein the signal choosing step comprises the step of selecting the pulsed signal having the following characteristics:

a square wave of at least about 0.1V in amplitude and about 1 μsec to 2 msec in duration.

5. The method according to claim 4 wherein the signal choosing step is carried out so each said signal pulse is repeated at least 0.1 Hz.

6. The method according to claim 1, wherein the signal choosing step is carried out by selecting a constant current pulsed signal as the pulsed signal.

7. The method according to claim 6, wherein the monitoring step is carried out by monitoring at least one voltage or impedance as the chosen electrical characteristic.

8. The method according to claim 6 wherein the signal choosing step comprises the step of selecting the pulsed signal having the following characteristics:

a square wave of at least about 0.1 mA in amplitude and about 1 μsec to 2 msec in duration.

9. The method according to claim 8 wherein the signal choosing step is carried out so each said signal pulse is repeated at least 0.1 Hz.

10. The method according to claim 1 wherein the determining step comprises the steps of:

measuring the magnitude of an initial rise in impedance as the chosen electrical characteristic for successive ones of said pulsed signals; and comparing said initial impedance rise magnitudes.

11. The method according to claim 1 wherein the determining step comprises the steps of:

measuring the magnitude of an initial change in the chosen electrical characteristic for successive ones of said pulsed signals; and comparing said initial change magnitudes.

12. The method according to claim 11 wherein the monitoring step is carried out by monitoring current as the chosen electrical characteristic and the measuring step is carried out by measuring an initial fall in the measured current as the initial change in the chosen electrical characteristic.

13. The method according to claim 11 wherein the monitoring step is carried out by monitoring impedance as the chosen electrical characteristic and the measuring step is carried out by measuring an initial rise in the impedance.

14. The method according to claim 1 wherein the determining step comprises the step of:

separating said chosen electrical characteristic into an ohmic impedance portion, corresponding to said leading edge portion, and a combined ohmic and capacitive impedance portion, corresponding to the following portion.

15. The method according to claim 14 wherein the determining step further comprises the step of:

measuring the slope of a chosen electrical characteristic versus time plot for an initial part of the combined ohmic and capacitive impedance portion for successive ones of said pulsed signals.

16. The method according to claim 14 wherein the determining step further comprises the step of:

measuring the maximum magnitude of the electrical characteristic for the ohmic impedance portion for successive ones of said signal pulses.

17. The method according to claim 14 wherein the determining step further comprises the step of:

measuring the average magnitude of the electrical characteristic for the combined ohmic and capacitive impedance portion for successive ones of said signal pulses.

18. The method according to claim 14 wherein the determining step further comprises the step of:

measuring a chosen magnitude of the electrical characteristic for the combined ohmic and capacitive impedance portion for successive ones of said signal pulses, said chosen magnitude measured at a chosen time following said leading edge portion.

19. The method according to claim 1, wherein the placing step is carried out within the heart of a patient.

20. The method according to claim 1, wherein the monitoring step is carried out automatically.

21. A method for determining electrode/tissue contact comprising the following steps:

selecting a pulsed signal pattern having one of the following characteristics:

(a) a square wave constant current DC signal pulse at least about 0.1 mA in amplitude and about 1 μsec to 2 msec in duration, each said signal pulse having a leading edge portion and a following portion;

(b) a square wave constant voltage DC signal pulse at least about 0.1V in amplitude and about 1 μsec to 2 msec in duration, each said signal pulse having a leading edge portion and a following portion;

applying a series of the signal pulses to an electrode;

placing the electrode into contact with a tissue site;

the placing step taking place with an ionic liquid covering the tissue site;

monitoring a chosen electrical characteristic at the electrode during a period of time before, during, and after the electrode contacts the tissue;

separating said chosen electrical characteristic for successive ones of said signal pulses into an ohmic impedance portion, corresponding to said leading edge portion, and a combined ohmic and capacitive impedance portion, corresponding to the following portion;

determining when the electrode contacts the tissue by at least one of the following:

(a) measuring the maximum magnitude of the chosen electrical characteristic for the ohmic impedance portion for successive ones of said signal pulses and comparing said maximum magnitudes;

(b) measuring the slope of a chosen electrical characteristic versus time plot for an initial part of the combined ohmic and capacitive impedance portion for successive ones of said signal pulses;

(c) measuring the magnitude of the combined ohmic and capacitive impedance portion for successive ones said signal pulses at a preselected time from said leading edge portion; and (d) measuring the average magnitude of the chosen electrical characteristic for a chosen portion of the combined ohmic and capacitive impedance portion for successive ones of the signal pulses; and choosing at least one of voltage, impedance or current as said chosen electrical characteristic.

22. Apparatus for determining electrode/tissue contact comprising:

a signal generator capable of generating signal pulses at a generator output;

an electrode electrically connected to the generator output;

means for measuring a value for a chosen electrical characteristic corresponding to a series of said signal pulses at the electrode before, during, and after the electrode contacts an ionic fluid-covered tissue;

means for comparing the measured values corresponding to said series of signal pulses; and means for providing an indication that said electrode has contacted the tissue based upon the compared measured values.

23. The apparatus according to claim 22 further comprising an electrophysiology catheter, the electrode being a part of the electrophysiology catheter.

24. The apparatus according to claim 22 wherein said signal generator is configured to create square wave, DC signal pulses.

25. The apparatus according to claim 22 wherein said signal generator is configured to create at least one of constant current and constant voltage signal pulses.

26. The apparatus according to claim 22 wherein said signal generator is configured to create a series of signal pulses each having the following characteristics:

constant current about 0.1 mA in amplitude for constant current signal pulses, constant voltage of at least about 0.1V in amplitude for constant voltage signal pulses; and said signal pulses being about 1 $\mu$sec to 2 msec in duration.

27. The apparatus according to claim 22 wherein said signal generator is capable of generating said series of signal pulses at a rate of at least about 0.1 Hz.

28. The apparatus according to claim 22 wherein said indication providing step further comprises means for displaying the amplitude of said values.

29. Apparatus for determining electrode/tissue contact comprising:

a signal generator capable of generating a series of signal pulses at a generator output, each said signal pulse having a chosen one of the following characteristics:

constant current at least about 0.1 mA in amplitude and about 1 $\mu$sec to 2 msec in duration; or constant voltage of at least 0.1V in amplitude and about 1 $\mu$sec to 2 msec in duration;

said signal generator being capable of generating said series of signal pulses at least about 0.1 Hz;

an electrophysiology catheter comprising an electrode electrically connected to the generator output;

means for determining a value for at least a chosen one of voltage, impedance or current as a measured electrical characteristic between the tissue and the electrode before, during, and after the electrode contacts the tissue;

said measured electrical characteristic for each said signal pulse comprising an ohmic impedance portion and a combined ohmic and capacitive impedance portion;

means for comparing said determined values corresponding to said series of signal pulses before, during, and after the electrode contacts the tissue; and means for providing an indication that said electrode has contacted the tissue based upon the determine values.

* * * * *